United States Patent [19]

Sugiura et al.

[11] Patent Number: 4,580,884

[45] Date of Patent: Apr. 8, 1986

[54] STAND APPARATUS FOR SUPPORTING MEDICAL INSTRUMENT

[75] Inventors: Yoshiyuki Sugiura, Hamamatsu; Mitugi Aoki, Tokyo, both of Japan

[73] Assignee: Tokyo Kogaku Kikai Kabushiki Kaisha, Tokyo, Japan

[21] Appl. No.: 545,136

[22] Filed: Oct. 25, 1983

[30] Foreign Application Priority Data

Oct. 28, 1982 [JP] Japan .............................. 57-163833[U]

[51] Int. Cl.[4] .............................................. A61B 3/00
[52] U.S. Cl. .................................................... 351/245
[58] Field of Search ................ 351/244, 245; 248/132, 248/161

[56] References Cited

FOREIGN PATENT DOCUMENTS 51101776 2/1950 Japan .
56-118604 9/1981 Japan .

*Primary Examiner*—Rodney B. Bovernick
*Attorney, Agent, or Firm*—Brumbaugh, Graves, Donohue & Raymond

[57] ABSTRACT

A stand apparatus for supporting a medical instrument such as ophthalmic instrument. The apparatus comprises a vertically movable arm, a guide rail for guiding the arm for vertical movement, a rod extending in parallel with the guide rail, and a braking device provided on the base portion of the arm and selectively engageable with the rod. The braking device includes; at least one braking member having at least two biting edges spaced from each other by a distance slightly greater than the diameter of the rod so as to bite the outer surface of the rod, the braking member swingably engaging at its one end with the base portion of the arm; a resilient spring for normally pressing the biting edges of the braking member into engagement with the outer surface of the braking member; a sliding arm member adapted to be moved by a brake releasing device in the direction perpendicular to the rod; and a link arm member to which the slide arm member and the other end of the braking member are connected pivotably.

7 Claims, 6 Drawing Figures

STAND APPARATUS FOR SUPPORTING MEDICAL INSTRUMENT

BACKGROUND OF THE INVENTION

1. Field of the Invention

The present invention relates to stand apparatus having vertically movable arms for supporting medical instruments such as ophthalmic stands, operating microscopes and roentgenographic equipments. More particularly, the present invention pertains to braking mechanisms for such vertically movable arms.

2. Description of the Prior Art

Ophthalmic stands are broadly used in ophthalmic hospitals, spectacle shops and so forth as an apparatus which suspends or mounts an ophthalmic instrument such as a refractor, refractometer or the like to locate such instrument at any desired positions with respect to a patient so that required tests can be performed. Such ophthalmic stands usually have vertically movable arm mechanisms including articulated arms for carrying heavy ophthalmic instruments such as refractometer, ophthalmometer and so forth. Among various types of such arms, the most popular one is of the balancing-weight type including a balancing weight which counterbalances the sum of the weight of the arm and the ophthalmic instrument carried by the arm.

Hitherto, two types of braking mechanism have been proposed and used for braking the arms for holding the latter at desired vertical positions. The braking mechanisms of the first type called "pedal-type braking mechanism" has a braking member which is incorporated in the arm mechanism and adapted to clamp, as a pedal is depressed, a guide rail along which the arm is moved vertically. The other type is the "solenoid-type braking mechanism" in which, as disclosed in Japanese Utility Model Laid-Open No. 56-118604, a braking member having an opening substantially of the same diameter as a guide rail is fitted around the guide rail with its one end held rotatably and, as a solenoid is energized, the braking member is attracted to contact at its inner surface with the guide rail thereby to prevent the liftable arm from moving vertically.

It should be noted that the pedal type braking mechanism is disadvantageous in that, since the pedal is mounted on the arm mechanism as a unit, the pedal is moved vertically as the arm is vertically moved so that it becomes quite difficult to depress the pedal by foot particularly when the pedal is at an elevated position. Usually, the arm mechanism comprises articulated and elongated arm and the ophthalmic instrument is carried at the free end of this arm, so that it has often been experienced that the pedal is spaced away from the position of the operator who manipulates the ophthalmic instrument. In such a case, the operator is obliged to move to a position where he can actuate the pedal.

The solenoid type braking mechanism is also disadvantageous in that it requires substantial electric power because the solenoid has to be energized during the operation of the ophthalmic instrument which takes much longer time than the movement of the arm. Further inconveniency is that when the ophthalmic stand is not used, the main switch of the instrument is turned off so that the brake also becomes inoperative. In this state, if the arm is of the balancing-weight type mentioned before, the arm is self-balanced and maintained stationary. In this condition, there may be a danger in that someone leans on the arm and falls down without being rigidly supported by the arm.

SUMMARY OF THE INVENTION

Accordingly, it is an object of the invention is to provide a stand apparatus for supporting medical instruments, having vertically movable arm means equipped with braking mechanism which is normally kept operative but becomes inoperative when the arm is being moved vertically.

Another object of the invention is to provide a stand apparatus provided with a balancing-weight type arm mechanism for supporting medical instruments, having an arm braking mechanism which is normally kept operative but becomes inoperative only when the arm is moved vertically and which can be made inoperative by the manipulation of a suitable means which is positioned within the reach of the operator.

To these ends, according to the invention, there is provided a stand apparatus for supporting a medical instrument comprising vertically movable arm means, guide rail means for guiding the arm means for vertical movements, rod means extending in parallel with the guide rail means, braking means provided on the liftable arm, said braking means including;

(a) at least one braking unit having at least two biting edges spaced with each other by a distance slightly greater than a diametrical dimension of the rod means and adapted to be brought into biting engagement with outer surface of the rod means, the braking unit being swingably supported at its one end by said arm means;

(b) resilient means for normally urging the biting edges into engagement with the outer surface of the rod means;

(c) sliding arm means adapted to be moved by brake releasing means in a direction perpendicular to the rod means; and (d) link arm means pivotably connected with the slide arm means and the other end of the braking unit.

Thus, the invention provides a stand apparatus for supporting medical instrument, equipped with vertically movable arm means associated with braking means having a satisfactory maneuverability, wherein the braking means is normally held operative to brake the arm so as to prevent any fall or heightwise shifting of the arm unless a brake releasing means is operated but is made inoperative to allow the arm to move vertically as desired by an operation of the releasing means which is located within the reach of the operator. This stand apparatus does not require electric power at all because the braking mechanism thereof is devoid of electric parts such as solenoid. For the same reason, the function of the stand apparatus of the invention is never affected by turning on and off of the main switch nor by the electric power failure.

DESCRIPTION OF THE PREFERRED EMBODIMENTS

Figure 1:
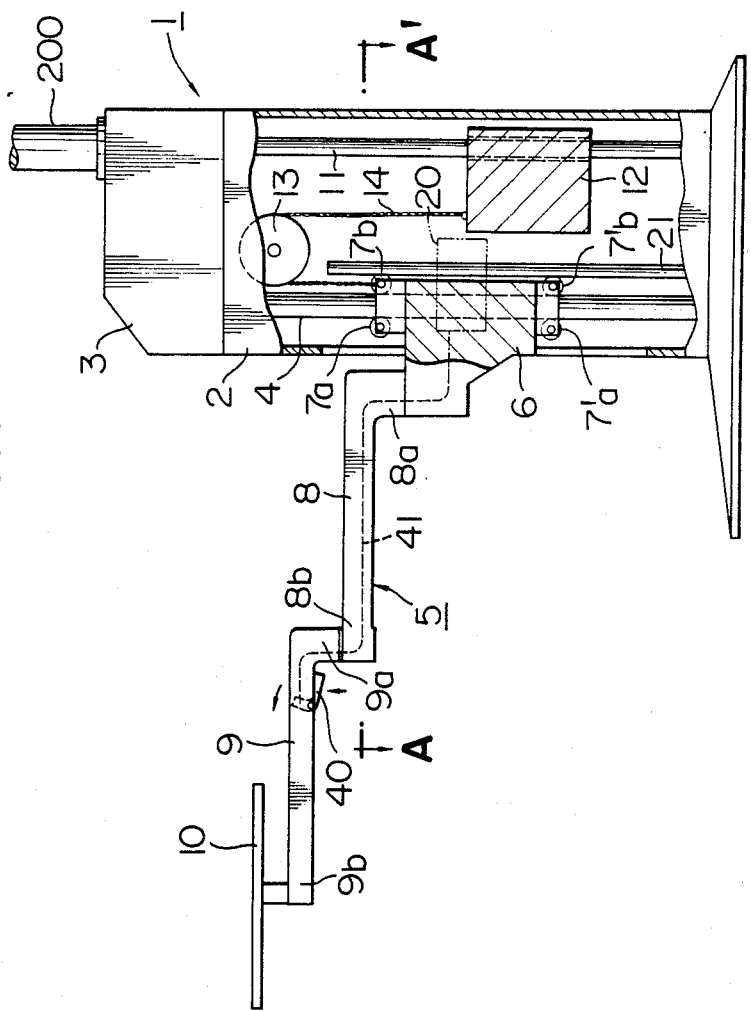
FIG. 1 is a partly-sectioned side elevational view of an ophthalmic stand as a first embodiment of the invention.
Figure 2:
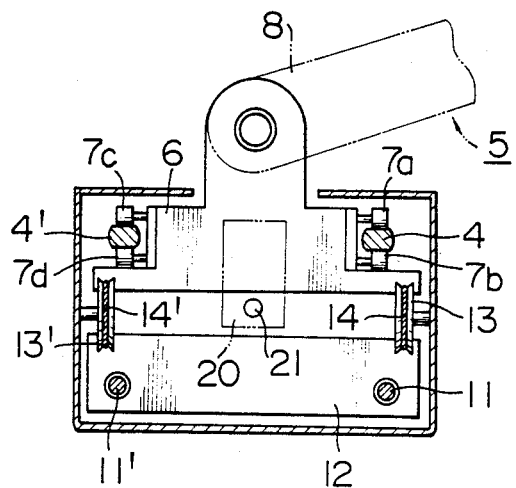
FIG. 2 is a sectional view taken along the line A-A' of FIG. 1.

Referring to the drawings, particularly to FIGS. 1 through 5, an ophthalmic stand as a first embodiment of the invention is generally designated at a reference numeral 1. The ophthalmic stand 1 has a column 2 to which secured are a control box 3 for controlling various instruments during an ophthalmic operation and a supporting post 200. A rockable main arm (not shown) is secured to an upper portion of the supporting post 200 for free rotation around the latter. A refractor is carried by the free end of the main arm.

A pair of vertical guide rails 4 and 4' are mounted in the column 2. Guide wheels 7a to 7d and 7'a to 7'd (only 7a to 7d are shown) secured to the base portion 6 of a liftable arm 5 making rolling contact with the side surfaces of the guide rails 4 and 4' so that the base portion 6 of the liftable arm can move up and down along the guide rails 4 and 4'. A first arm 8 and a second arm 9 are swingably connected to the base portion 6 through respective articulates 8a, 8b and 9a so as to constitute a multi-articulated arm. A table 10 is rotatably secured to the end 9b of the second arm 9. An ophthalmic instrument such as a refractometer is mounted on the table 10.

A pair of weight guides 11 and 11' are secured to the column 2 to run in parallel with the guide rails 4 and 4'. A balancing weight 12 is held by the weight guides 11 and 11' for sliding motion up and down along the latter. The balancing weight 12 is connected to the base portion 6 of the liftable arm by means of wires 14 and 14' which go round pulleys 13 and 13' which are rotatably secured to side surfaces of the column. The arrangement is such that the balancing weight 12 and the liftable arm 5 carrying the instrument balance each other.

Figure 3:
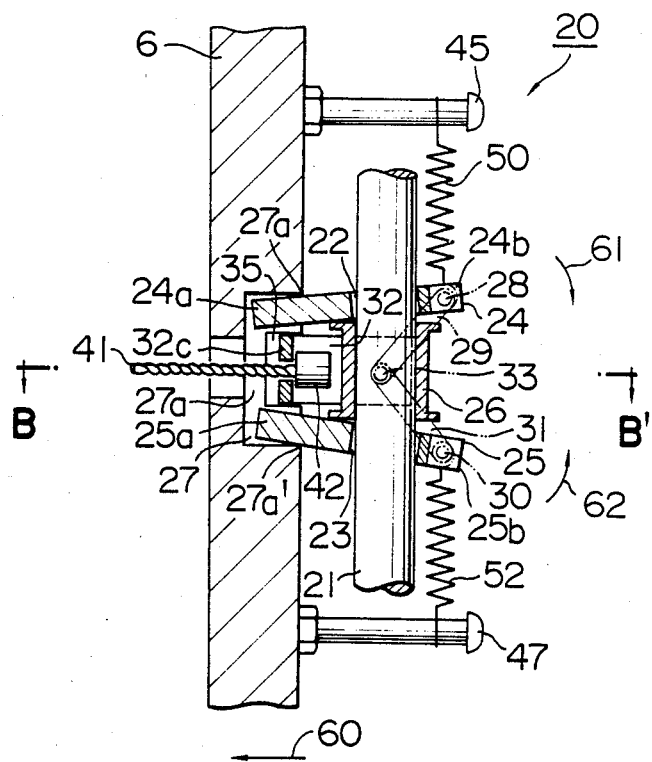
FIG. 3 is a vertical sectional view of a braking mechanism incorporated in the first embodiment.
Figure 4:
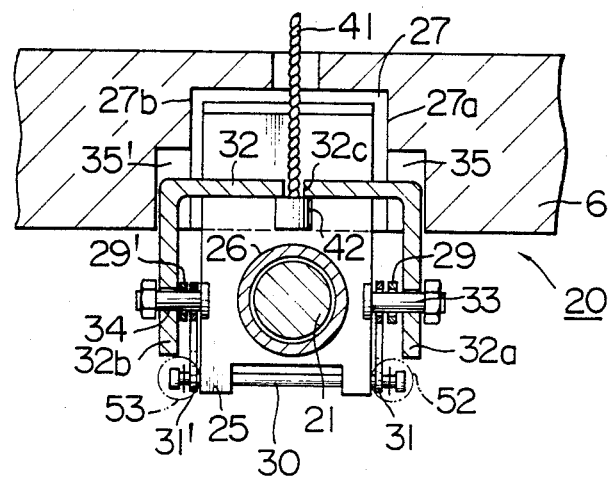
FIG. 4 is a sectional view taken along the line B-B' of FIG. 3.
Figure 5:
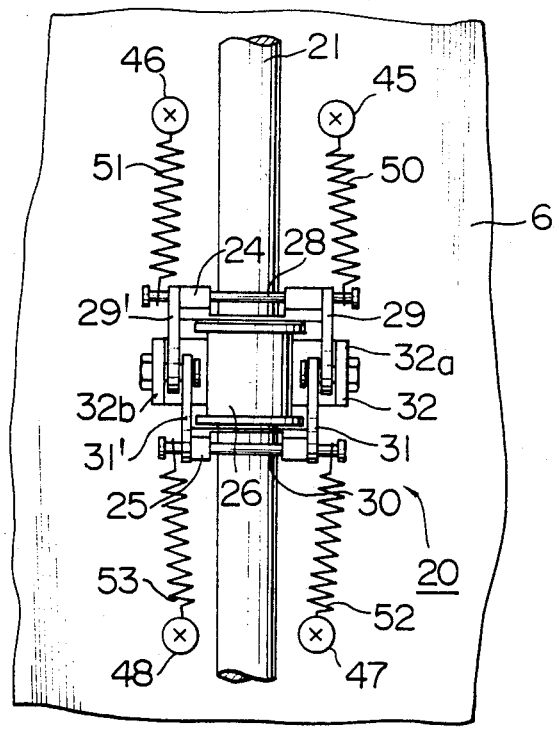
FIG. 5 is a front elevational view of the brake mechanism incorporated in the first embodiment.

An explanation will be given hereinunder as to the detail of a braking mechanism 20 incorporated in the base portion 6 of the liftable arm 5, with specific reference to FIGS. 3-5. FIG. 3 is a vertical sectional view of the braking mechanism 20, FIG. 4 is a sectional view taken along the line B-B' of FIG. 3, and FIG. 5 is a front elevational view of the braking mechanism 20. The braking mechanism 20 has a rod 21 disposed in the column so as to extend in parallel with the guide rails 4 and 4', and braking members 24 and 25 having bores 22 and 23 of a diameter slightly greater than the diameter of the rod 21. The braking members 24 and 25 thus loosely fit around the rod 21 such that a collar 26 fitting around the rod 21 is sandwiched between the braking members 24 and 25. The braking members 24 and 25 have one ends 24a and 25a which are received by a recess 27 formed in the base portion 6 so that the braking members 24 and 25 are swingable around fulcrums constituted by the edges 27a and 27a' of the recess 27. A shaft 28 is secured to the other end 24b of the braking member 24. Link arms 29 and 29' are rotatably secured at their one ends to respective ends of the shaft 28. Similarly, link arms 31 and 31' are rotatably connected at their one ends to respective ends of a shaft 30 which is secured to the other end 25b of the braking member 25. The other ends of the link arms 29 and 31 are rotatably secured to a shaft 33 which in turn is attached to an arm 32a of a slide arm 32. Similarly, the other ends of the link arms 29' and 31' are rotatably secured to a shaft 34 which in turn is attached to the other arm 32b of the slide arm 32. The arms 32a and 32b of the slide arm 32 have base end portions which are slidably received by guide grooves 35 and 35' formed in a wall 27b of the recess 27 in the base portion 6 of the slidable arm 5. The slide arm 32 is provided with a hole 32c for attaching a wire. A wire 41 is connected at its one end to an operation lever 40 (see FIG. 1) rotatably secured to the second arm 9, while the other end of the wire 41 is inserted into the hole 32c in the slide arm 32. A stopper 42 connected to the other end of the wire 41 prevents the same from being withdrawn from the hole 32c. Springs 50 to 53 are retained at their one ends by bolts 45 to 48 which are screwed to the base portion 6. The other ends of the springs 50 to 53 are retained by both ends of the shafts 28 and 30.

In the braking mechanism 20 having the described construction, the braking members 24 and 25 are normally urged rotatingly upward and downward, respectively, around the fulcrums constituted by the edges 27a and 27a' of the recess, by the tensile force produced by the springs 50 to 53, so that the inner peripheral surfaces of the braking members 24 and 25, i.e. the wall surfaces of the bores 22 and 23, make pressure contact with the peripheral surface of the rod 21 so as to bite and grip the rod 21. In this state, the base portion 6 of the liftable arm 5 having this braking mechanism 20 cannot move along the guide rails, so that the liftable arm 5 is prevented from moving up and down.

For releasing the brake, the operator grips the second arm 9 to lift the operation lever 40 upwardly, so that the slide arm 32 slides along the guide grooves 35 and 35' as indicated by an arrow 60. The movement of the slide arm 32 causes a movement of the link arms 29 to 31'. However, since the braking members 24 and 25 connected to these link arms are prevented from moving by the edges 27a and 27a' of the recess 27, these braking members 24 and 25 are swung as indicated by arrows 61 and 62, repectively, around these edges 27a and 27a' overcoming the tensile force of the springs 50 to 53. Since the bores 22 and 23 in the braking members 24 and 25 have a diameter greater than the outside diameter of the rod 21, so that the braking members 24 and 25 release the rod 21 as they are swung as explained above. In this state, the arm 5 can be moved up and down by quite a small manual force because the weight of the arm and the instrument thereon is balanced by the weight of the balancing weight 12.

Although a first embodiment of the invention has been described with specific reference to an ophthalmic stand, this is not exclusive and the invention can be applied to other uses than the ophthalmic stand. It is to be understood also that the construction of the described embodiment can be modified in various ways.

Figure 6:
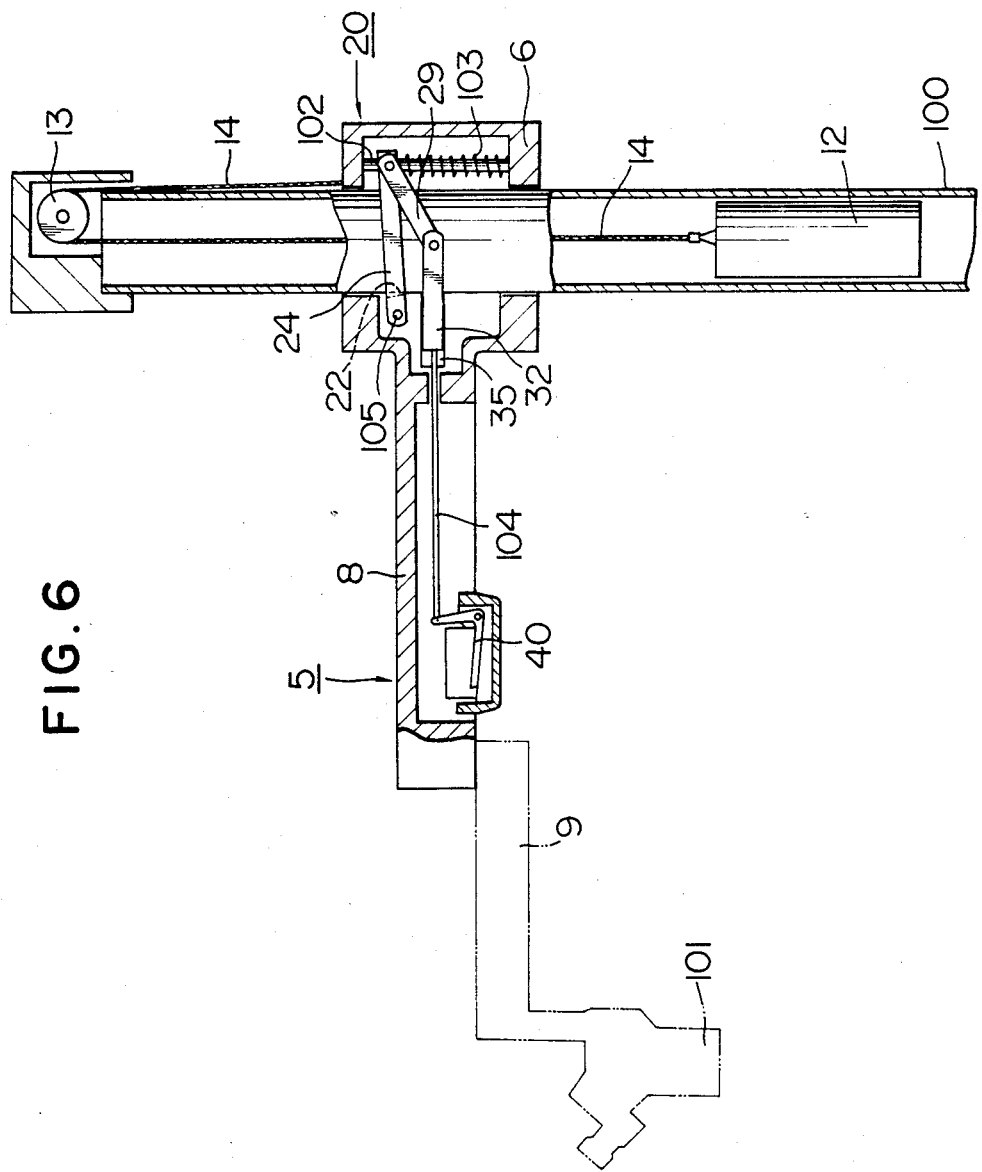
FIG. 6 is a partly-sectioned side elevational view of a second embodiment of the invention.

FIG. 6 is a vertical sectional view of a second embodiment applied to a floor-type stand for supporting an operating microscope. In the following description, the same reference numerals are used to denote the same parts or members as those used in the first embodiment, and the detailed description of such parts or members is omitted to avoid duplication of explanation.

The stand has a tubular supporting post 100 receiving a balancing weight 12 which is connected through a wire 14 going around a pulley 13 to the base portion 6 of a first arm 8 which is adapted to slide up and down along the outer surface of the supporting post 100. A microscope unit 101 is suspended from the first arm 8 through an arm which may be a second arm 9. A braking mechanism 20 of a construction substantially same as that in the first embodiment is incorporated by the base portion 6. The braking mechanism 20 of the second embodiment is distinguished from that of the first embodiment in that the supporting post 100 plays also the role of the rod 21 of the first embodiment. Namely, when the movement of the liftable arm is not necessary, the bore 22 in the braking member 24 is strongly pressed against the supporting post 100 by the force of a compression spring 103 fitted around a guide rod 102 in the base portion 6, so that the base portion 6 is prevented from moving along the supporting post 100. In this embodiment, the wire 41 for connecting the operation lever 40 to the slide arm 32 in the first embodiment is substituted by a bar 104. In addition, the braking member 24 in this embodiment is adapted to swing around a pin 105 provided on the base portion of the liftable arm.

In operation, the operation lever 40 is rotated to move the slide arm 32 through the action of the bar 104. The movement of the slide arm 32 is converted into the rotation of the braking member 24 through the link arm 29 thereby to disengage the wall of the bore 22 in the braking member 24 from the supporting post 100 so as to release the brake as in the case of the first embodiment.

What is claimed is:

1. In a stand apparatus for supporting a medical instrument from a liftable arm extending outwardly from and mounted for movement on a longitudinal rod, braking means provided on the liftable arm comprising:

at least one braking unit having biting edge means which in one angular position relative to the longitudinal rod brings the biting edge means into locking engagement with the longitudinal rod and in another angular position relative to the longitudinal rod moves the biting edge means into release position, one said braking unit being supported at one end by the liftable arm for angular adjustment relative to the axis of the longitudinal rod;

resilient means normally urging the braking unit into an angular position which locks the liftable arm in engagement with the longitudinal rod;

a slide arm carried by the liftable arm for sliding movement in a direction perpendicular to the axis of the longitudinal rod;

link arm means connecting the slide arm and the braking unit so that movement of the slide arm adjusts the angular position of the braking unit from locking to release position;

an actuatable brake releasing lever carried by the liftable arm at a distance from the longitudinal rod; and a wire connecting the releasing lever and the slide arm to slide the arm to adjust the angular position of the braking unit from locking to releasing position.

2. Braking means as set forth in claim 1 in which said braking unit has at least two biting edges spaced from each other by a distance slightly greater than the diameter of the longitudinal rod and in which both biting edges are adapted to be brought into biting engagement with the outer surface of the longitudinal rod in the locking position.

3. Braking means as set forth in claim 1 in which said braking unit has one end received in a recess formed in a base portion of the liftable arm and including an edge of said recess which serves as a fulcrum for the braking unit so that it can be adjustably rocked from locking to releasing position.

4. Braking means as set forth in claim 1 including at least a pair of braking units and a collar fitted on said longitudinal rod intermediate the braking units.

5. In a standing apparatus as set forth in claim 1 including a counterbalancing weight connected with the liftable arm, a flexible connection between the counterbalancing weight and the liftable arm and a pulley rotatably supported to receive the flexible connection.

6. Braking means as set forth in claim 2 in which said biting edges are constituted by peripheral edges of a bore formed in the braking unit and in which said longitudinal rod is accommodated within said bore.

7. Braking means as set forth in claim 1 including at least a pair of braking units, angularly adjustable through said link arm means toward each other to a releasing position and away from each other to a locking position.

* * * * *